(12) United States Patent
Atsumori et al.

(10) Patent No.: US 8,229,531 B2
(45) Date of Patent: Jul. 24, 2012

(54) OPTICAL BIOINSTRUMENTATION DEVICES

(75) Inventors: Hirokazu Atsumori, Kawagoe (JP);
Masashi Kiguchi, Kawagoe (JP);
Atsushi Maki, Fuchu (JP); Michiyuki Fujiwara, Kashiwa (JP)

(73) Assignee: Hitachi Medical Corporation, Tokyo (JP)

( * ) Notice: Subject to any disclaimer, the term of this patent is extended or adjusted under 35 U.S.C. 154(b) by 194 days.

(21) Appl. No.: 11/914,701

(22) PCT Filed: Feb. 13, 2006

(86) PCT No.: PCT/JP2006/302436
§ 371 (c)(1),
(2), (4) Date: Nov. 16, 2007

(87) PCT Pub. No.: WO2006/123457
PCT Pub. Date: Nov. 23, 2006

(65) Prior Publication Data
US 2009/0088616 A1    Apr. 2, 2009

(30) Foreign Application Priority Data
May 18, 2005    (JP) ................................. 2005-144848

(51) Int. Cl.
*A61B 5/1455* (2006.01)
(52) U.S. Cl. ........................................ 600/344; 600/340
(58) Field of Classification Search .................. 600/340, 600/344
See application file for complete search history.

(56) References Cited

U.S. PATENT DOCUMENTS

| | | | | |
|---|---|---|---|---|
| 4,321,930 | A * | 3/1982 | Jobsis et al. ................... | 600/344 |
| 6,510,274 | B1 * | 1/2003 | Wu et al. ........................ | 385/137 |
| 7,190,986 | B1 * | 3/2007 | Hannula et al. ................ | 600/344 |
| 7,702,374 | B2 * | 4/2010 | Ishizuka et al. ................ | 600/344 |
| 2004/0054271 | A1 | 3/2004 | Maki et al. | |
| 2004/0236226 | A1 * | 11/2004 | Maki et al. ..................... | 600/473 |
| 2006/0058594 | A1 | 3/2006 | Ishizuka et al. | |

FOREIGN PATENT DOCUMENTS

| | | |
|---|---|---|
| JP | 5-93403 | 12/1993 |
| JP | 8-117209 | 5/1996 |
| JP | 9-98972 | 4/1997 |
| JP | 9-149903 | 6/1997 |
| JP | 2001-286449 | 10/2001 |

(Continued)

OTHER PUBLICATIONS

Office Action issued in Japanese Patent Application No. 2007-516205 on Aug. 17, 2010.

*Primary Examiner* — Eric Winakur
(74) *Attorney, Agent, or Firm* — Antonelli, Terry, Stout & Kraus, LLP.

(57) ABSTRACT

There is provided an optical bioinstrumentation device, with which measurement data reflect more correctly the information inside the living body with less noise even the subject moves when the information inside the living body is measured by using the light.
In the present invention, the means for fixing the part other than the tips of the optical fibers for irradiation and detection on the fixing member which is to fix the tips of the optical fiber for irradiation and detection on the subject, or, the means for fixing the optical fiber is fixed on the fixing member which is to fix the end of the optical fiber on the subject, or the means for fixing the optical fiber at two or more positions on the subject.

5 Claims, 21 Drawing Sheets

FOREIGN PATENT DOCUMENTS

| | | |
|---|---|---|
| JP | 2003-339677 | 12/2001 |
| JP | 2002-11012 | 1/2002 |
| JP | 2002-291751 | 10/2002 |
| JP | 2003-322612 | 11/2003 |
| JP | 2004-248961 | 9/2004 |
| JP | 2004-205493 | 7/2007 |
| WO | WO 2004052211 A1 * | 6/2004 |
| WO | WO 2005/058161 A1 | 6/2005 |

* cited by examiner

[Figure 1]
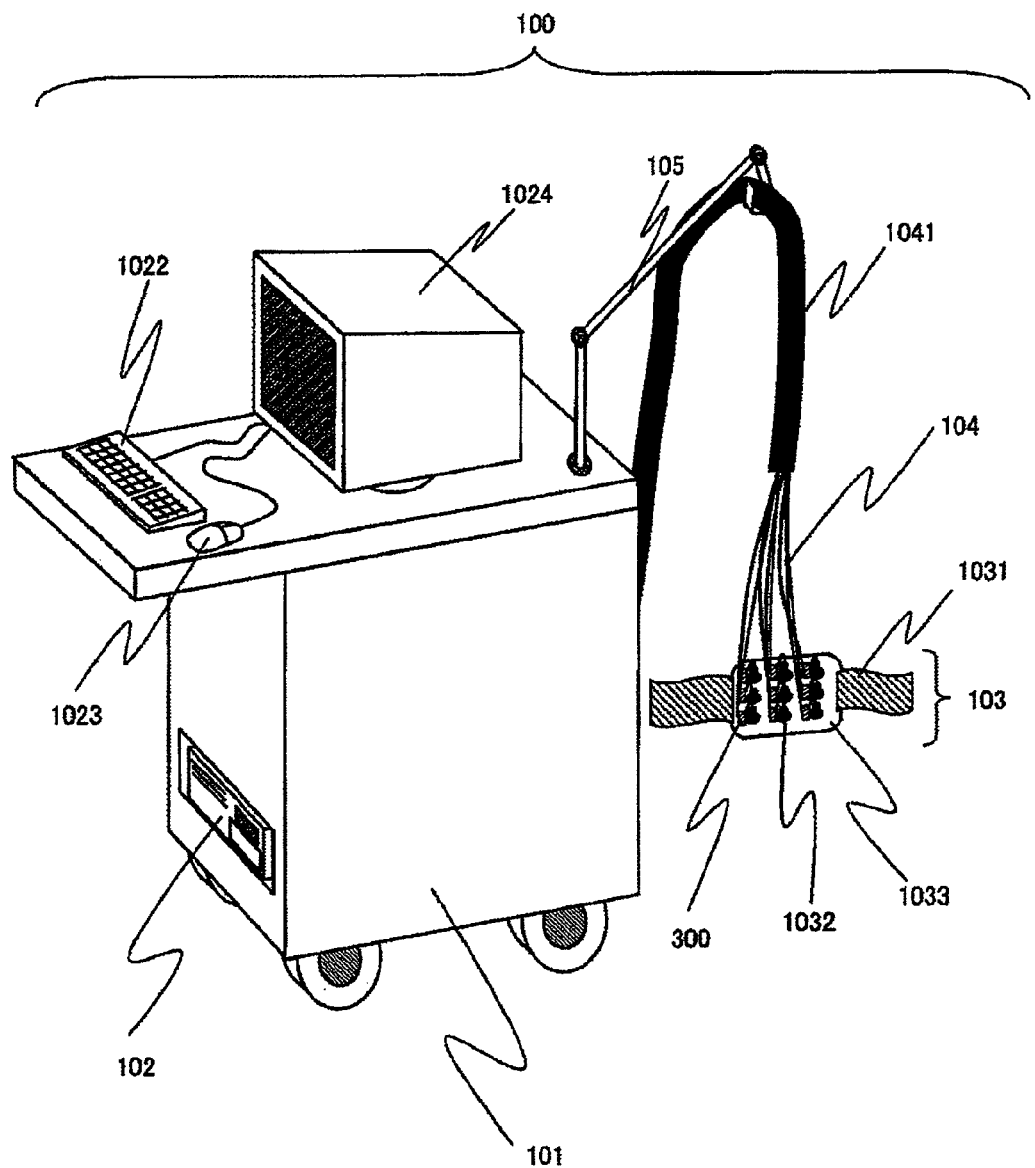

[Figure 2]
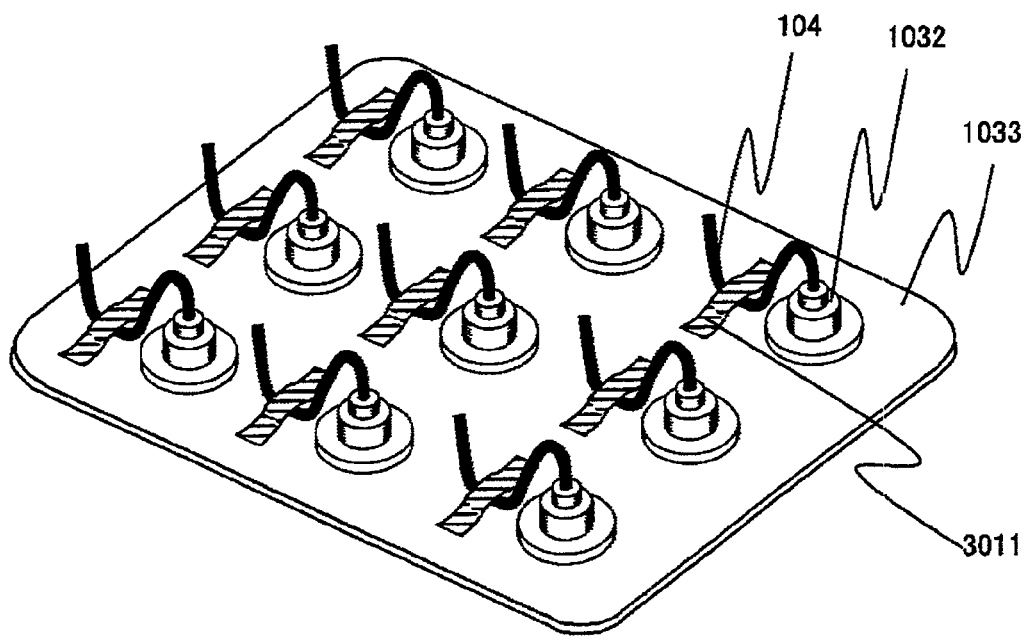
[Figure 3]
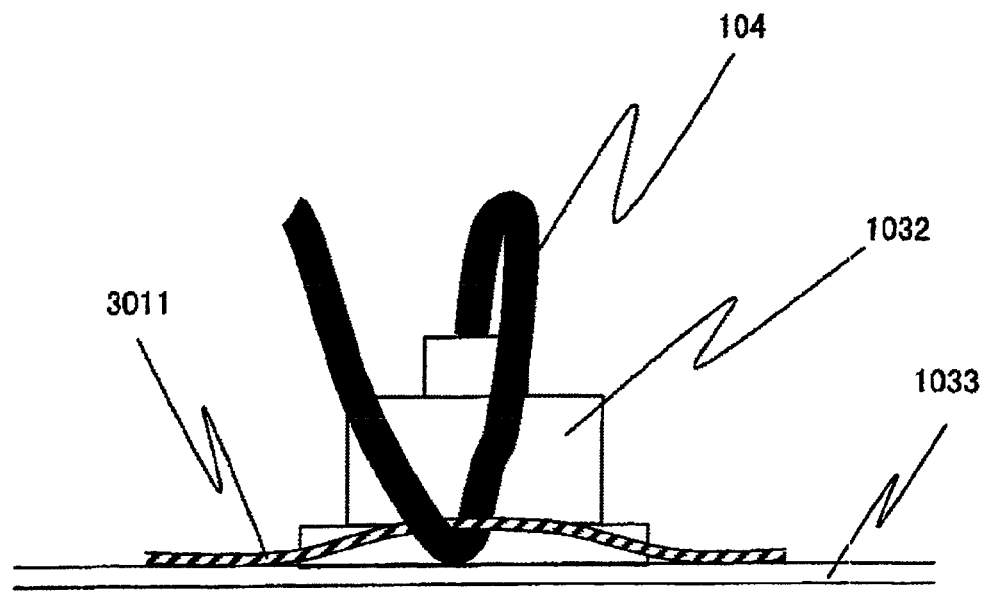

[Figure 4]
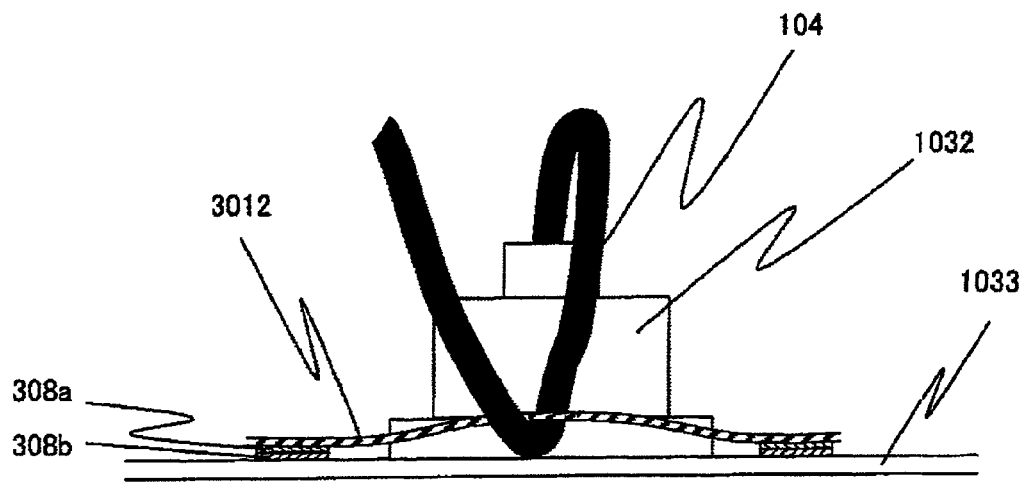
[Figure 5]
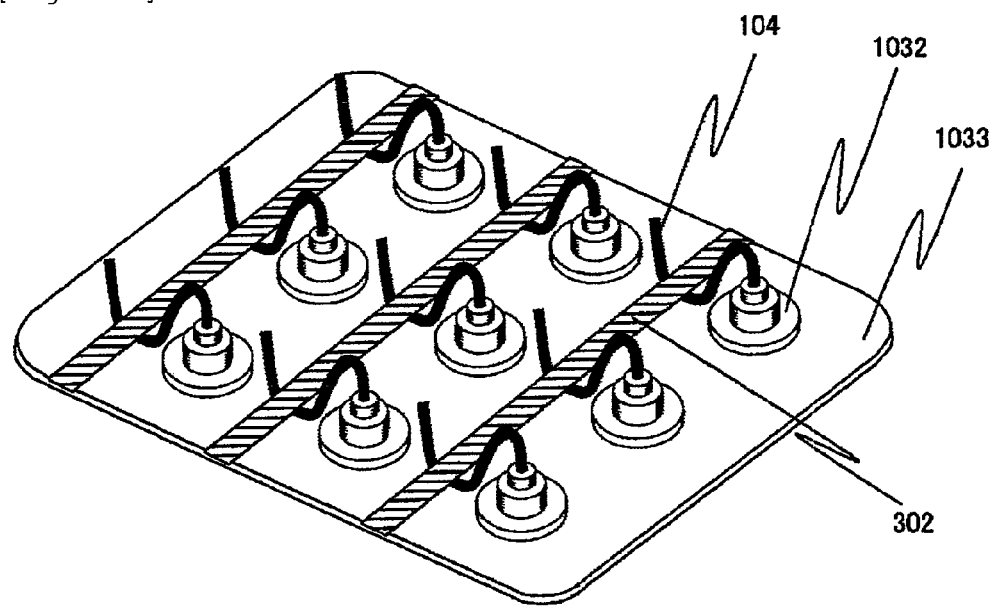

[Figure 6]
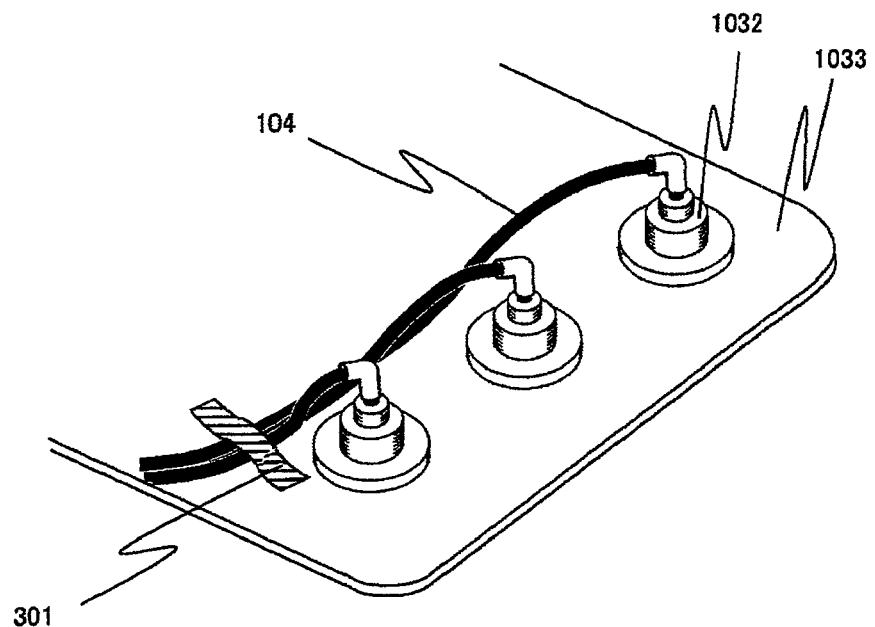
[Figure 7]
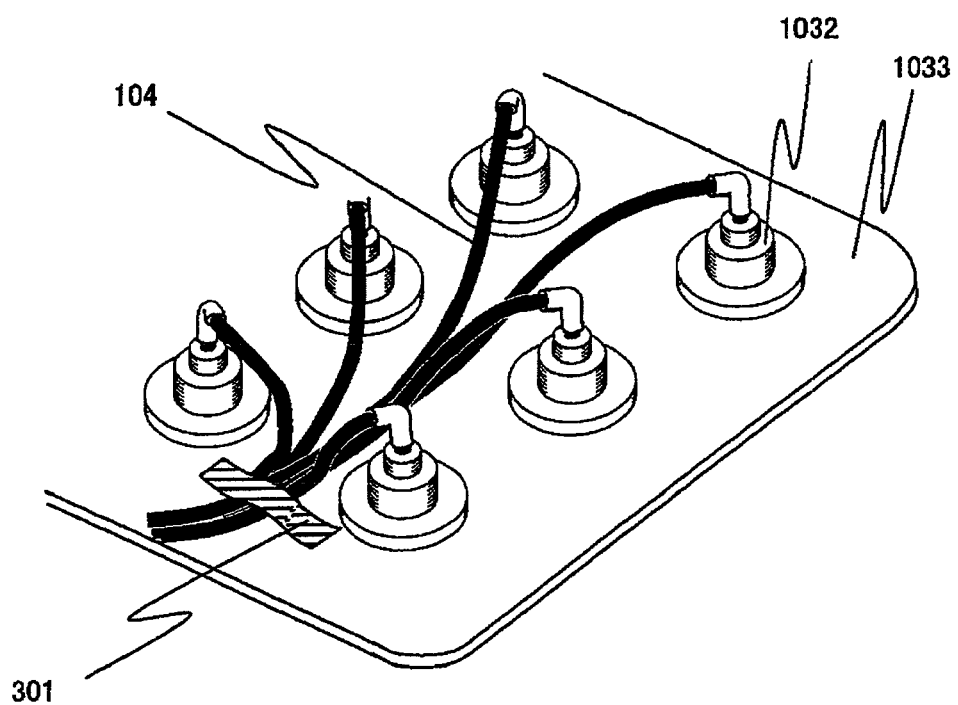

[Figure 8]
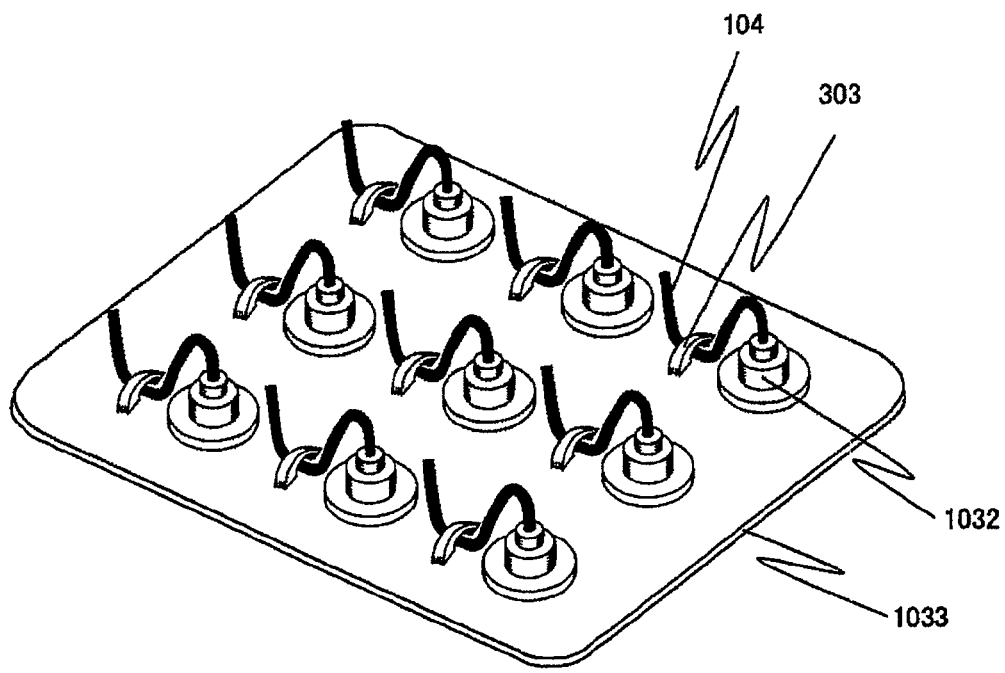
[Figure 9]
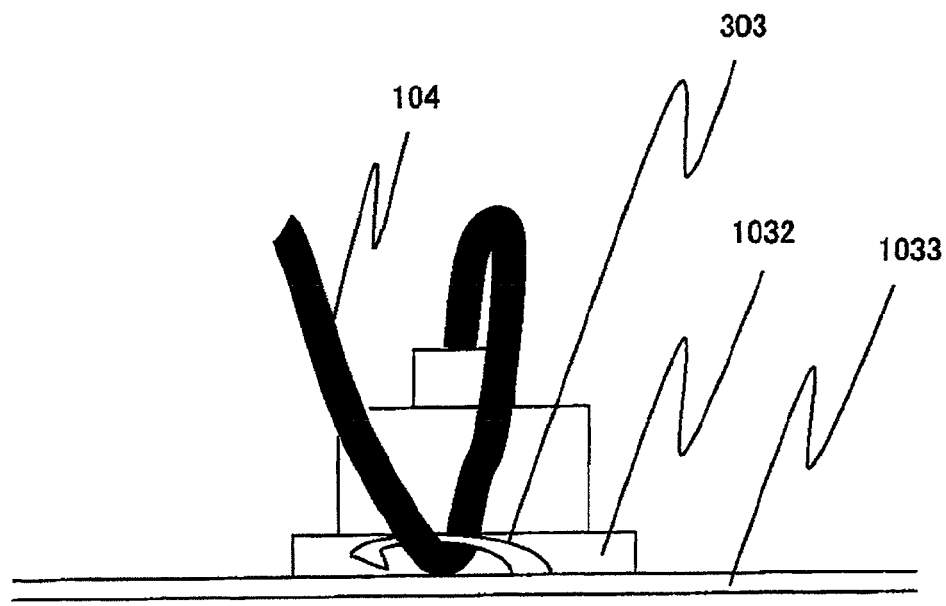

[Figure 10]
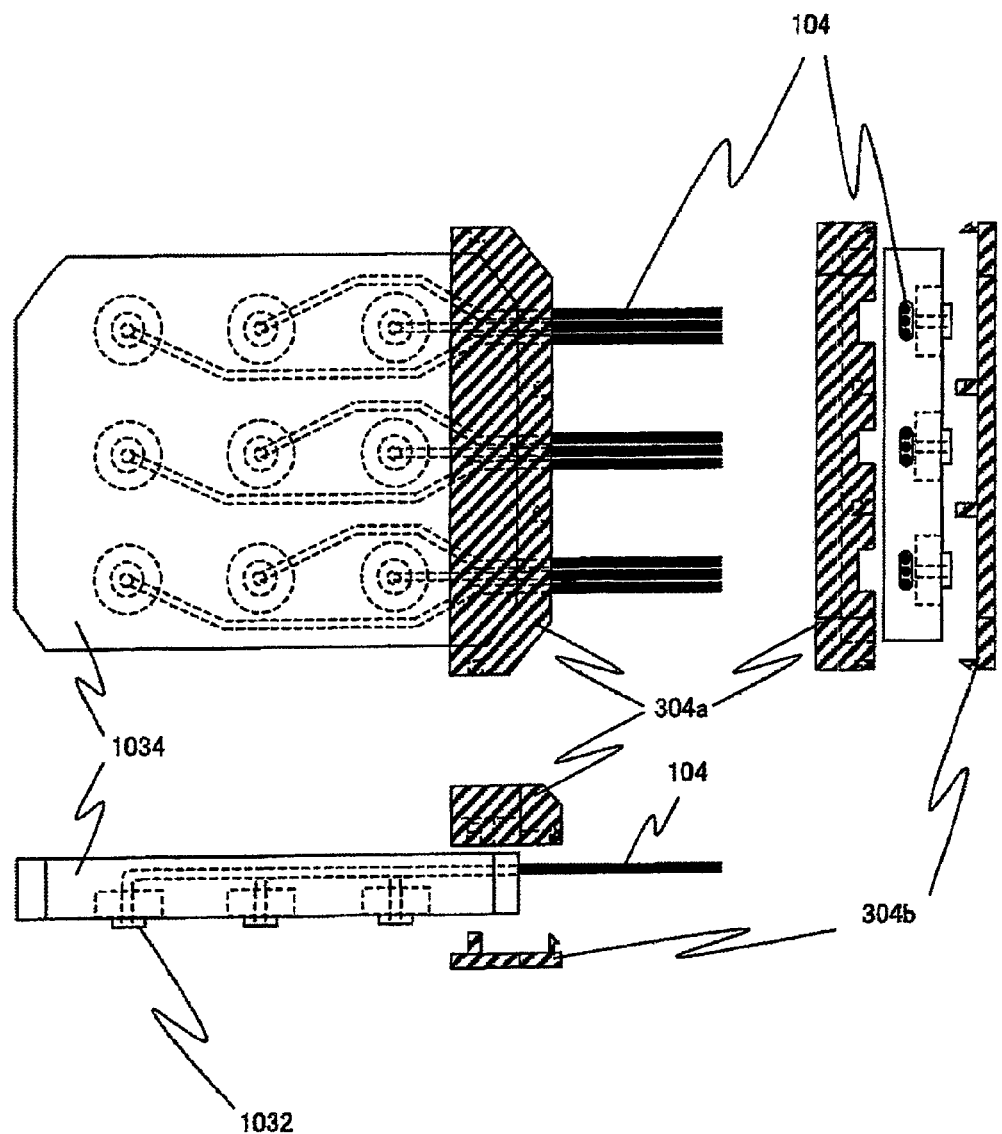

[Figure11]
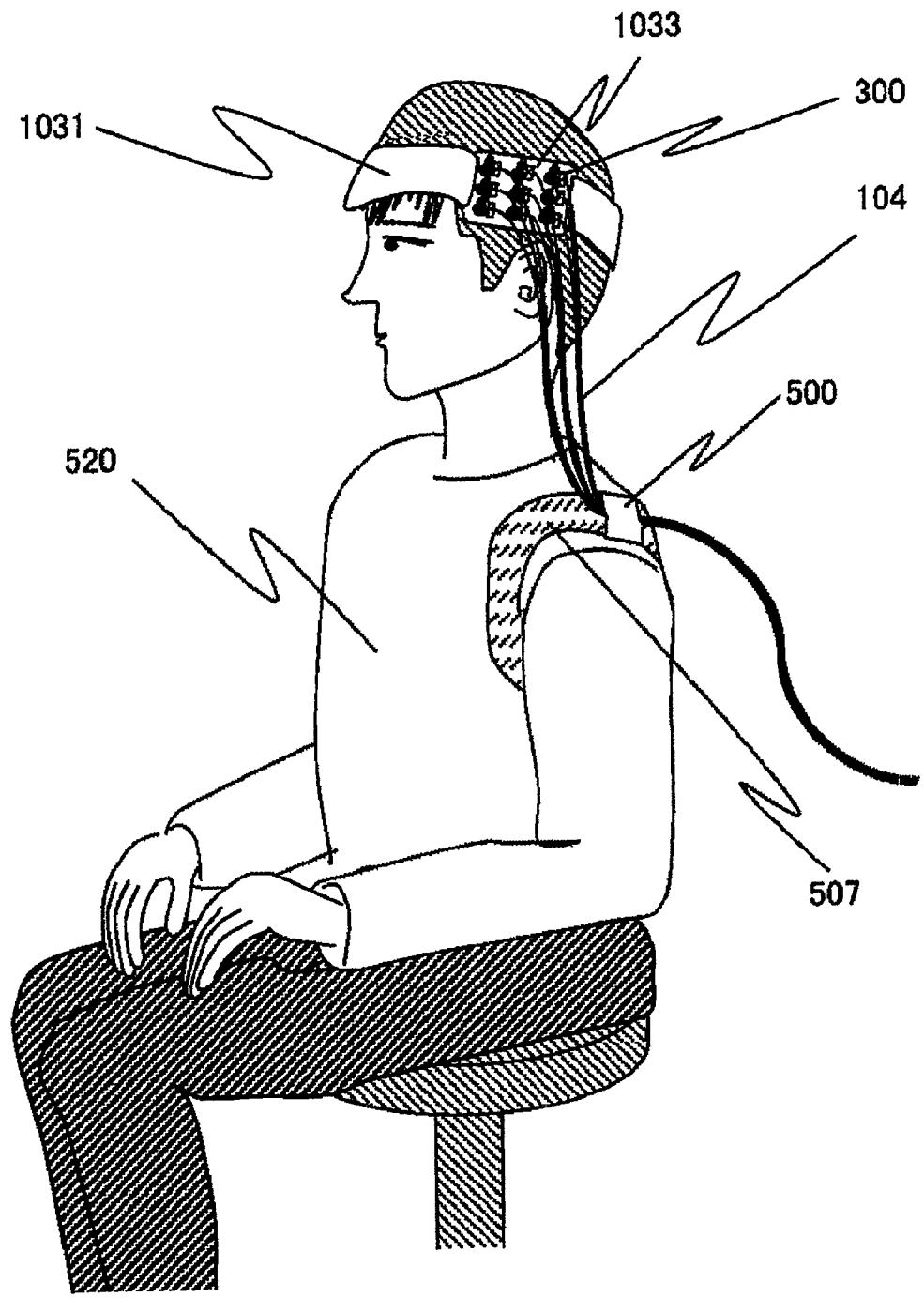

[Figure 12]
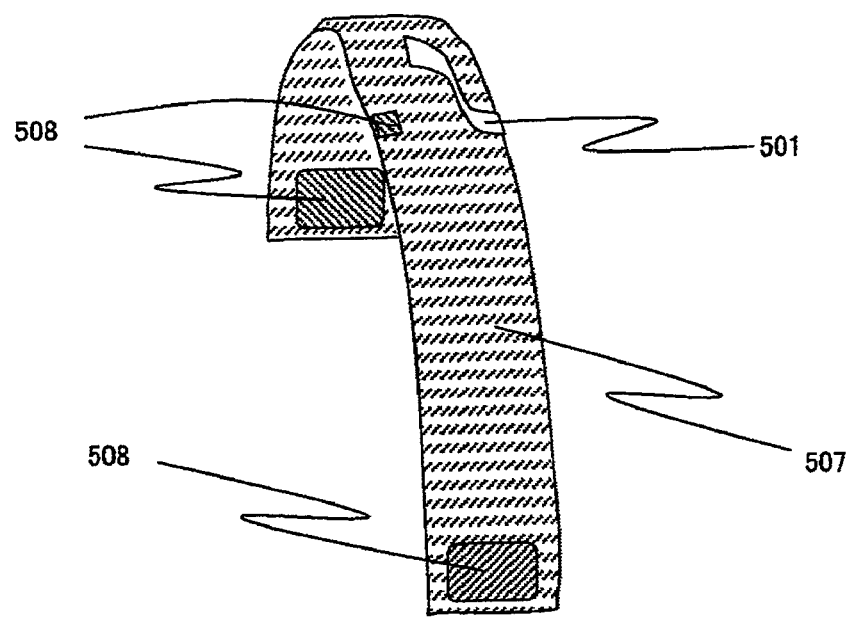
[Figure 13]
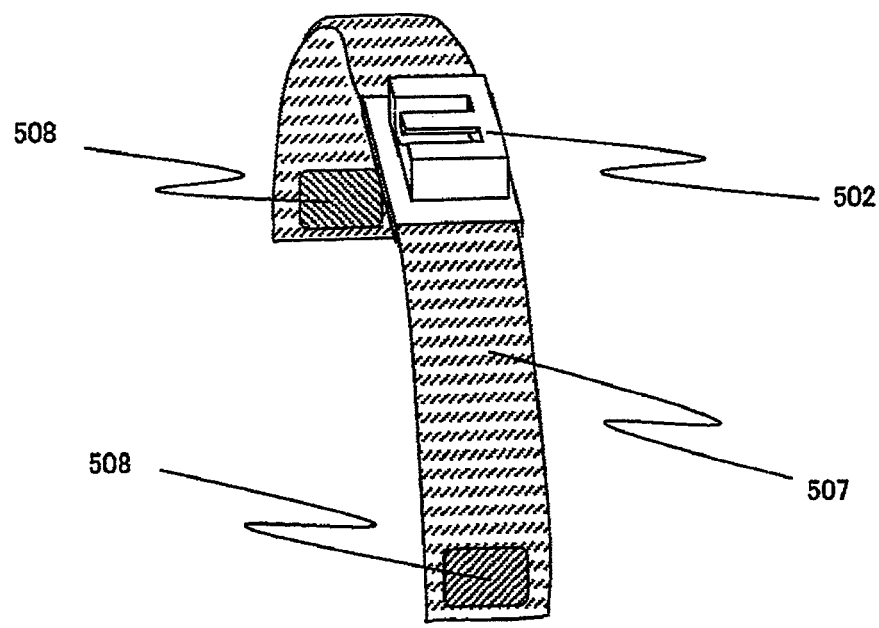

[Figure 14]
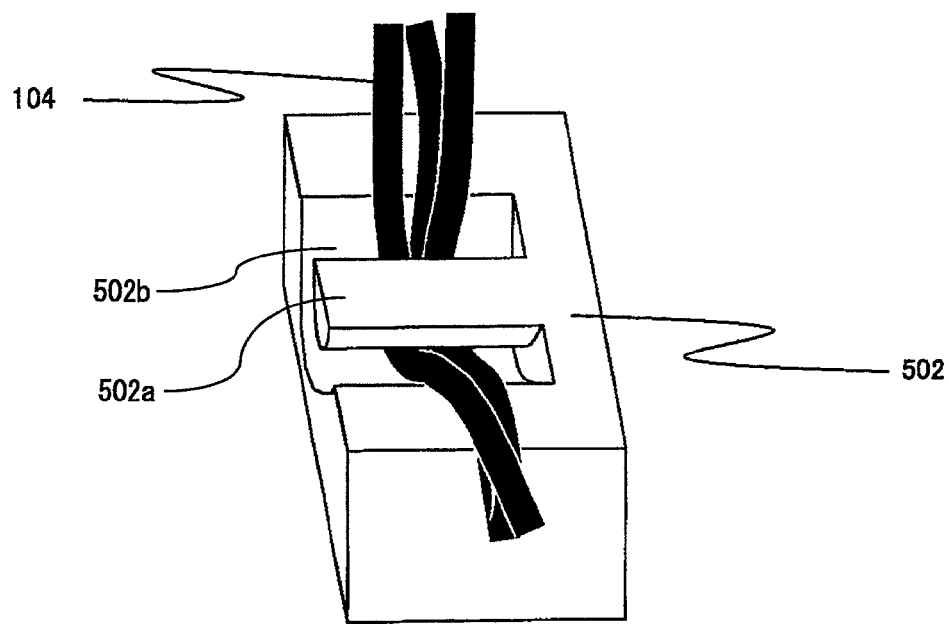
[Figure 15]
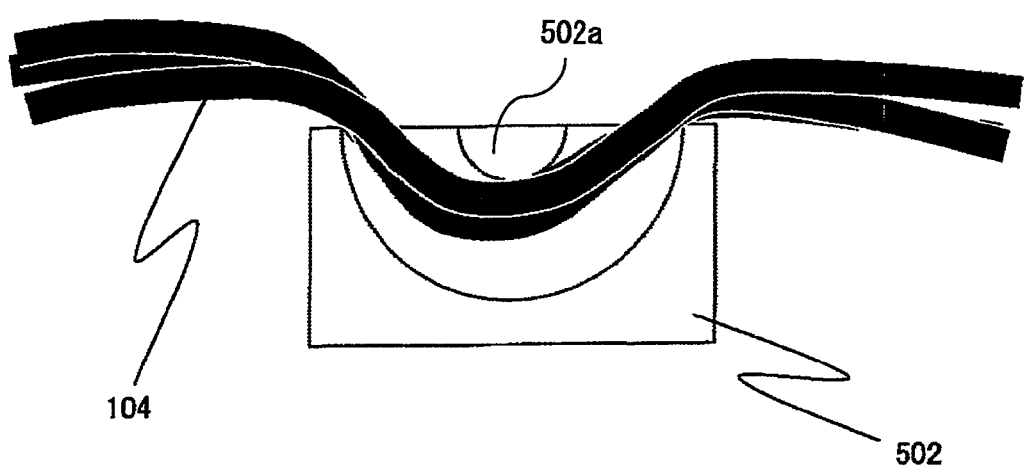

[Figure 16]
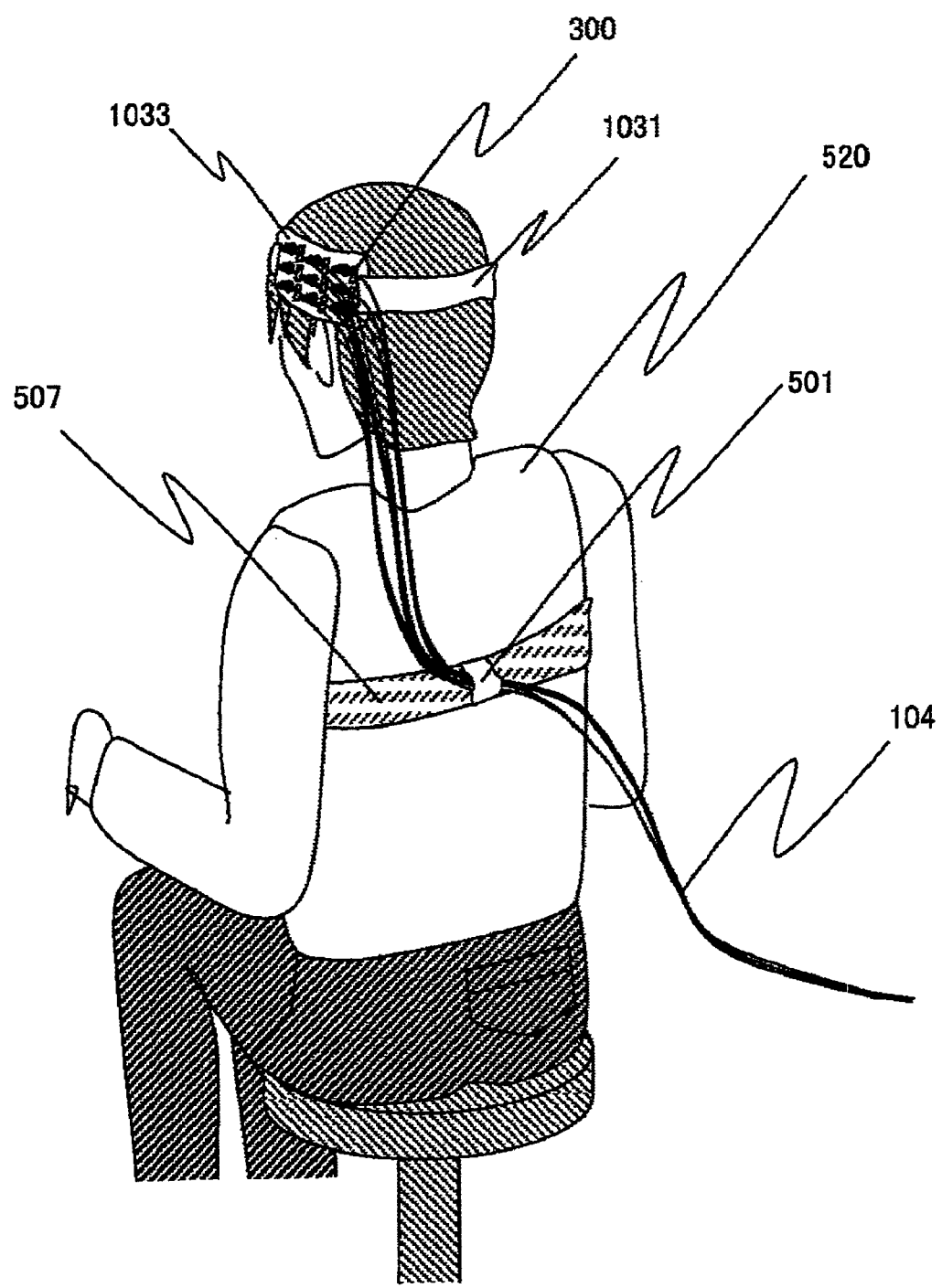

[Figure 17]
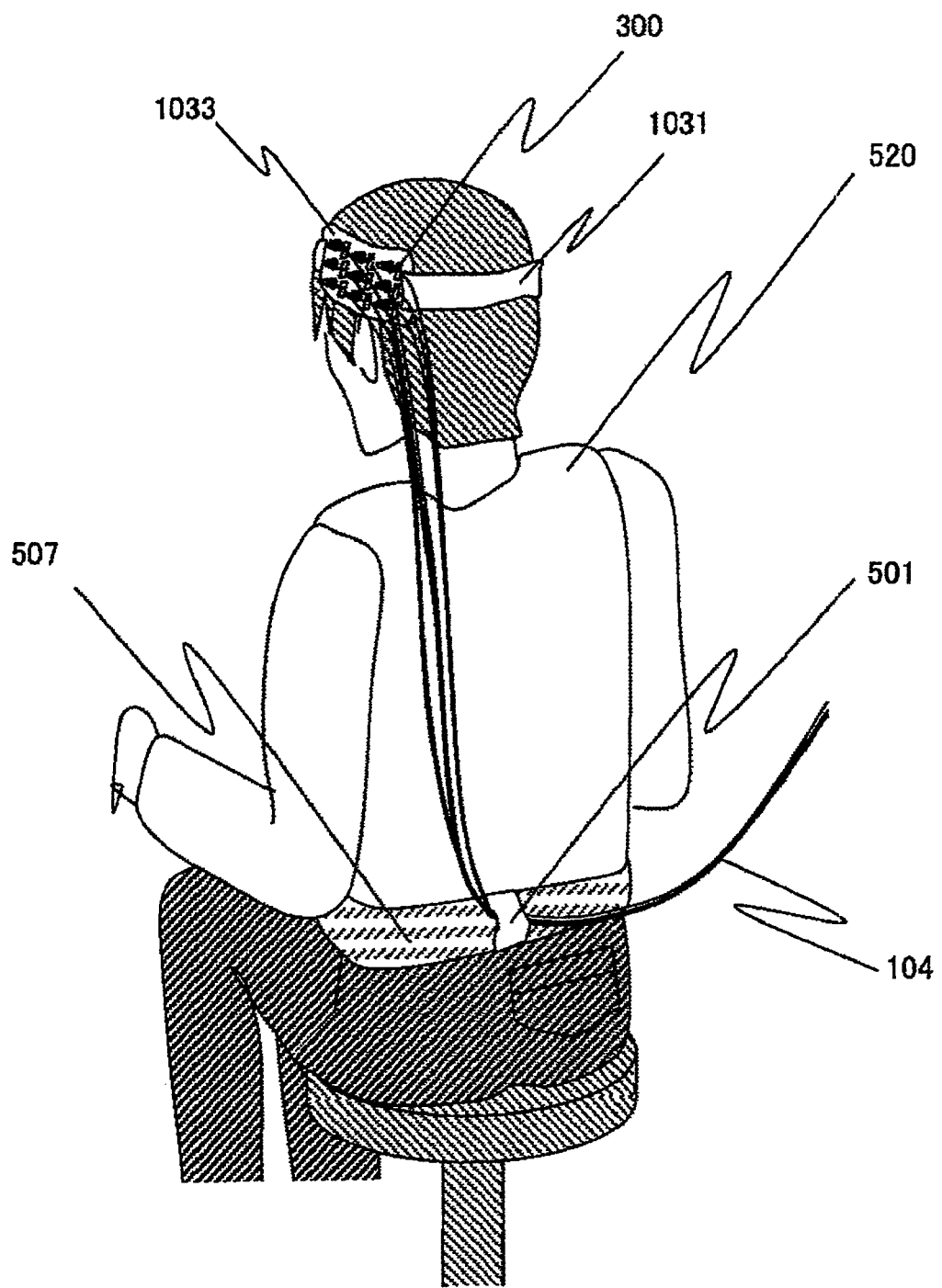

[Figure 18]
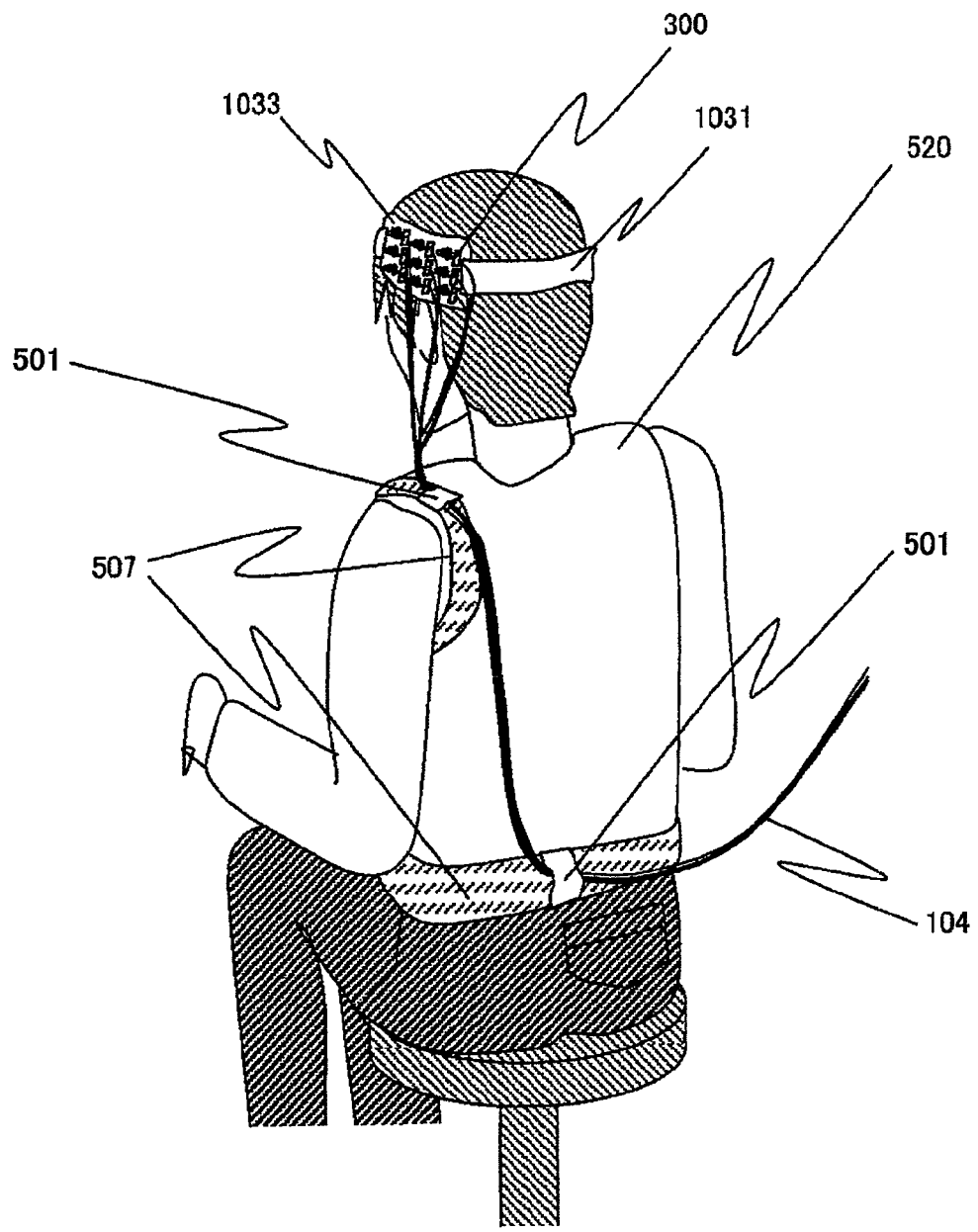

[Figure 19]
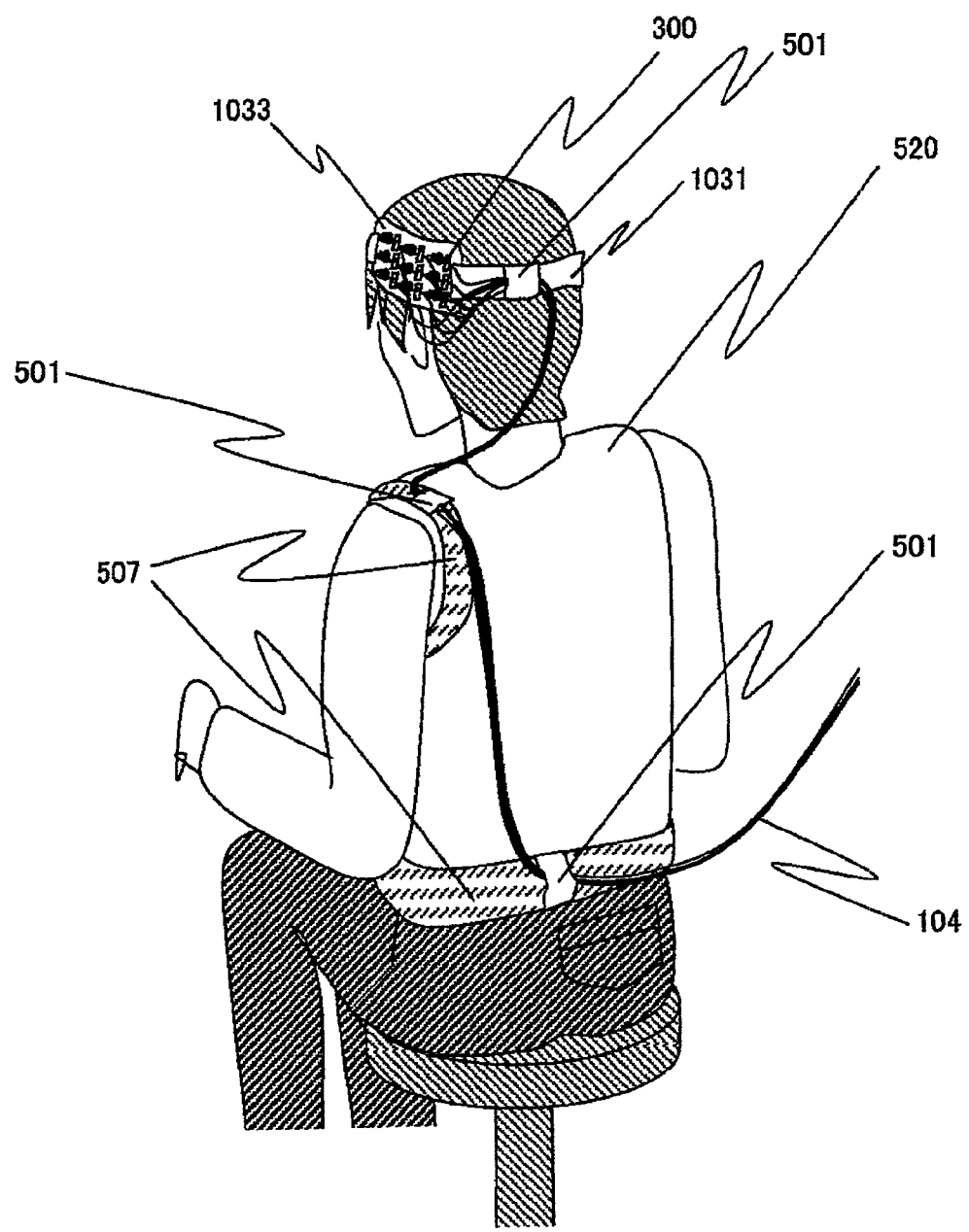

[Figure 20]
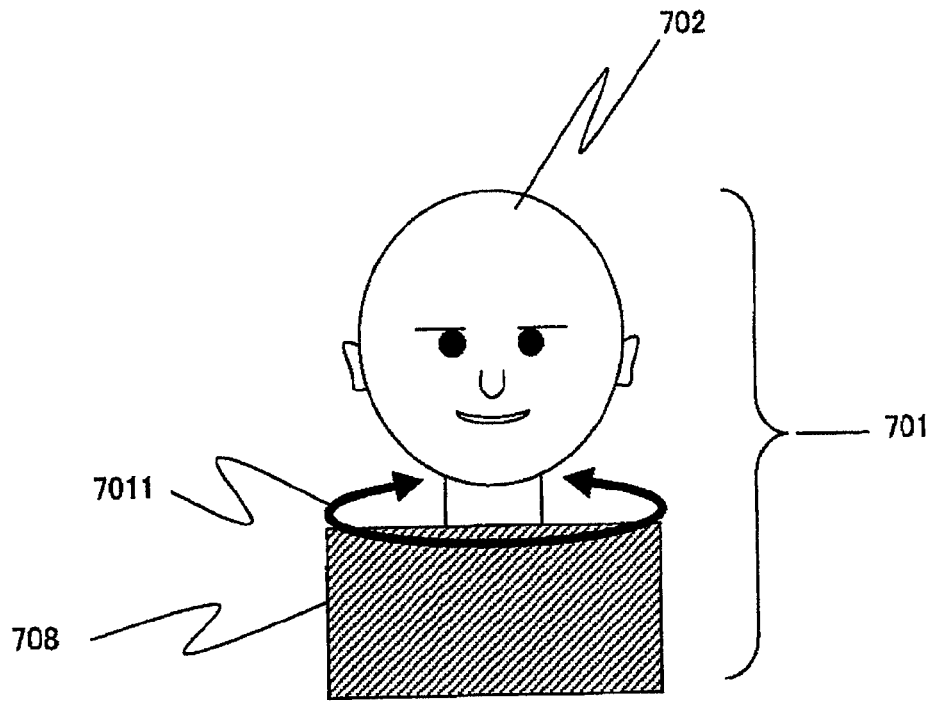
[Figure 21]
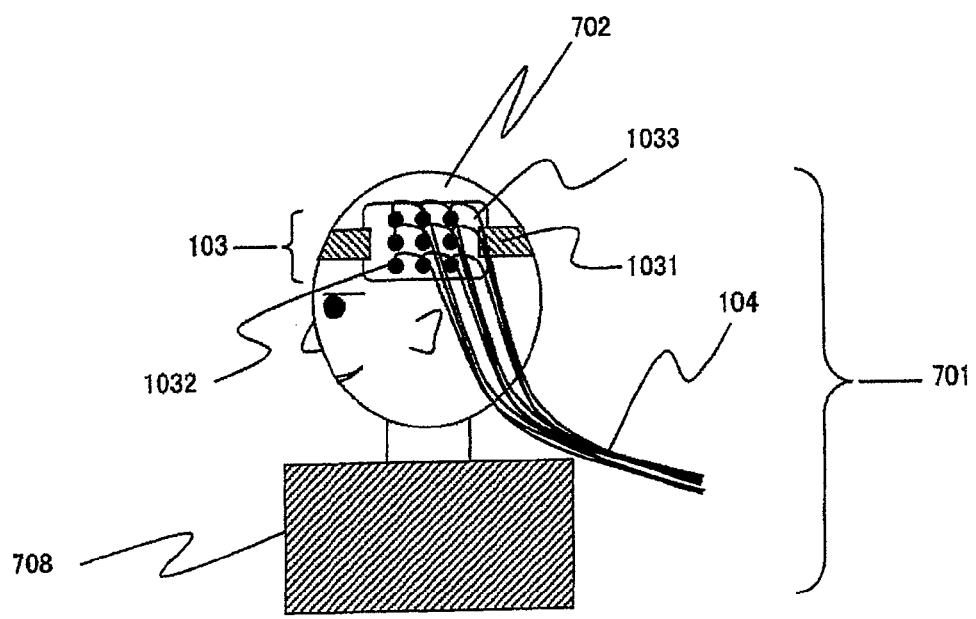

[Figure 22]
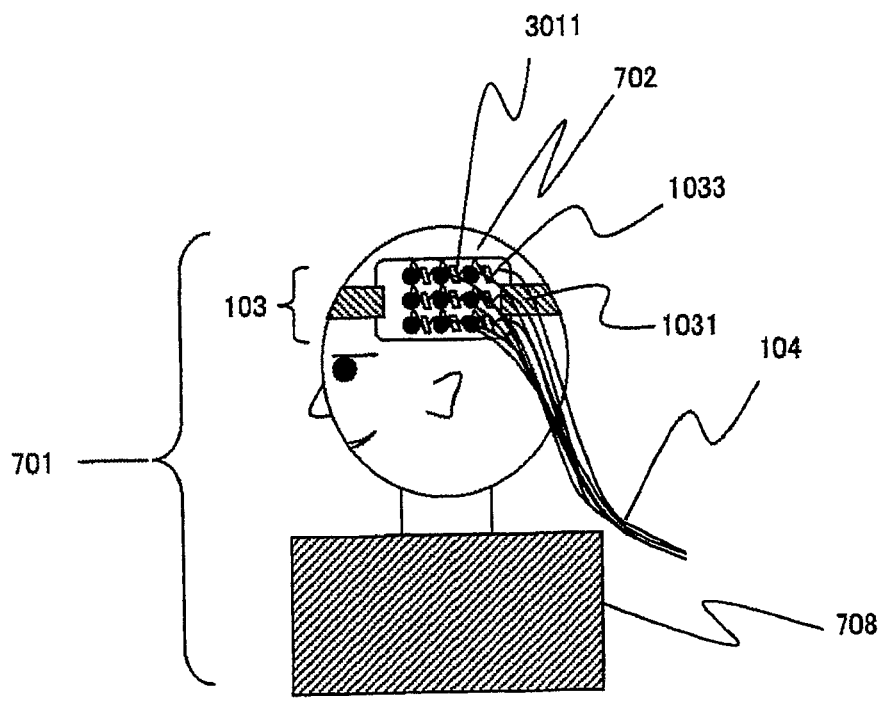
[Figure 23]
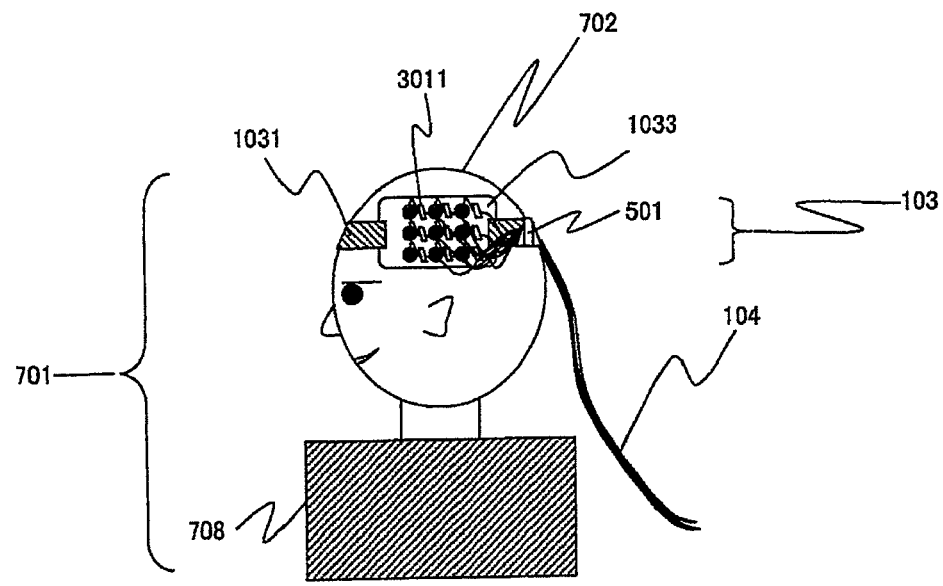

[Figure 24]
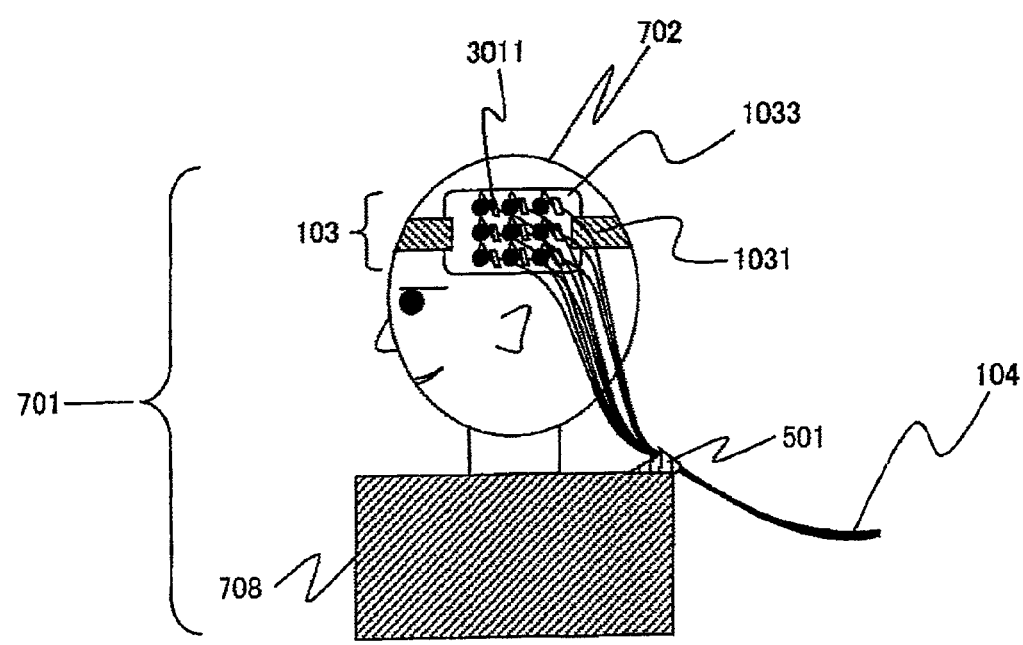

[Figure 25]
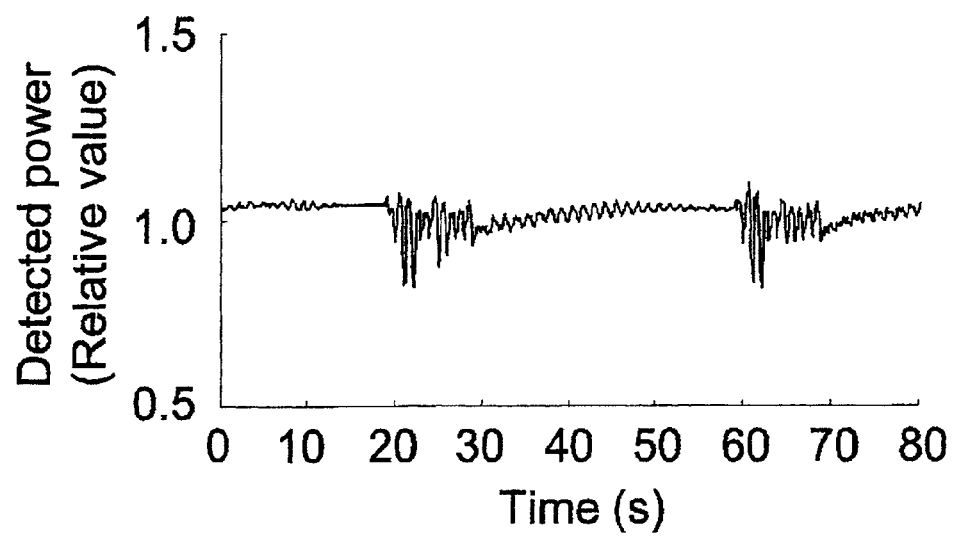
[Figure 26]
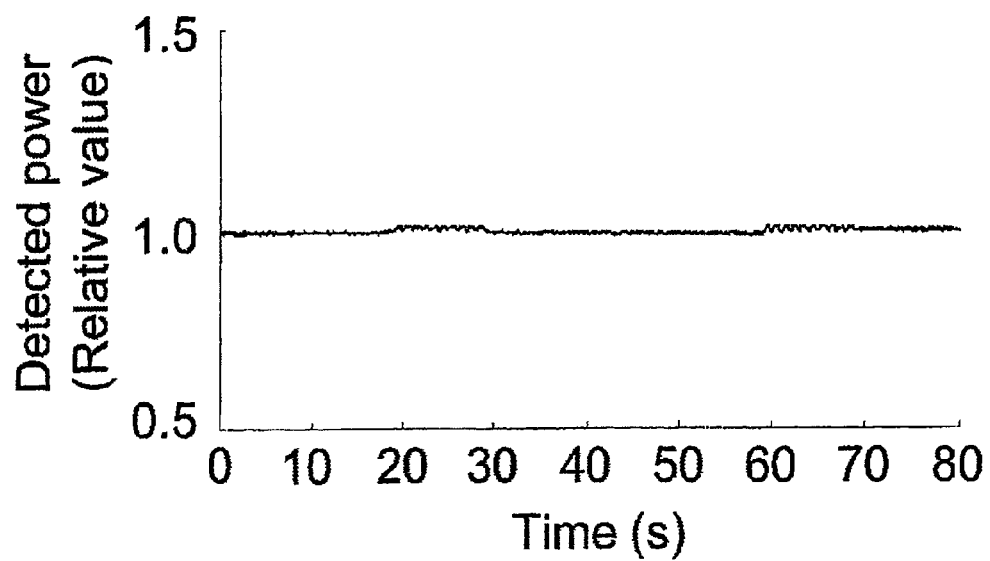

[Figure 27]
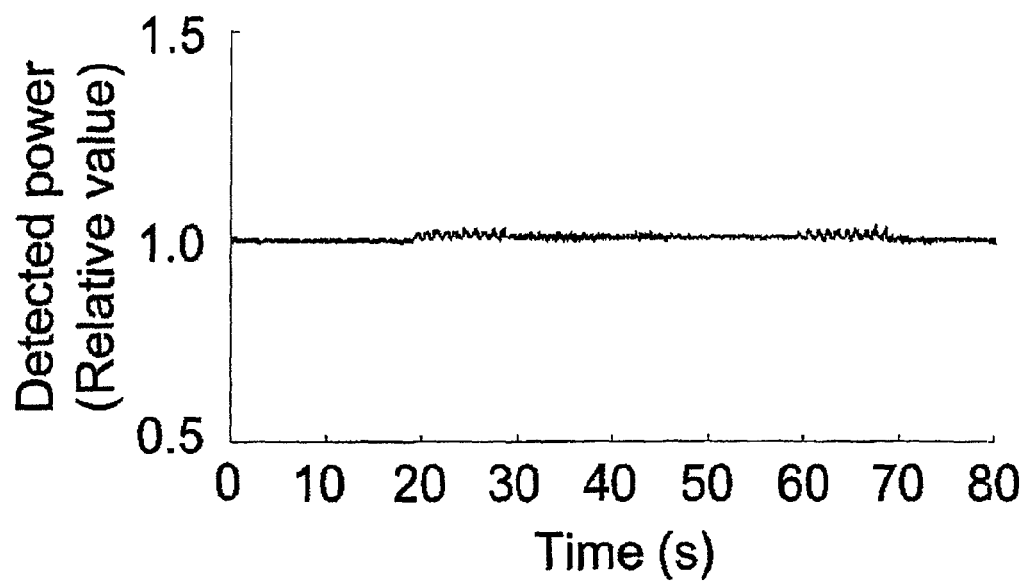
[Figure 28]
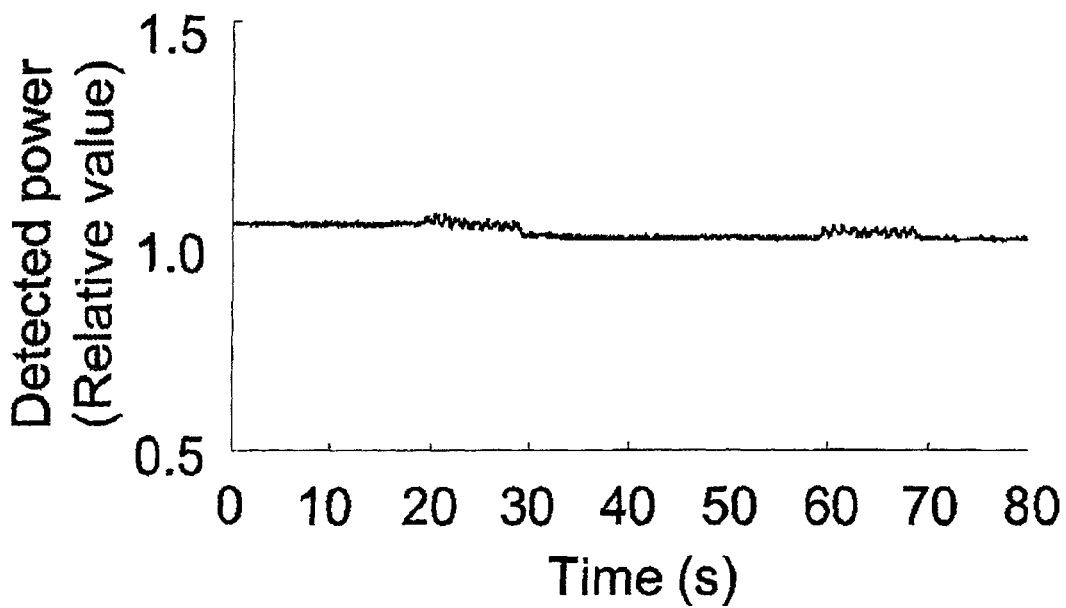

[Figure 29]
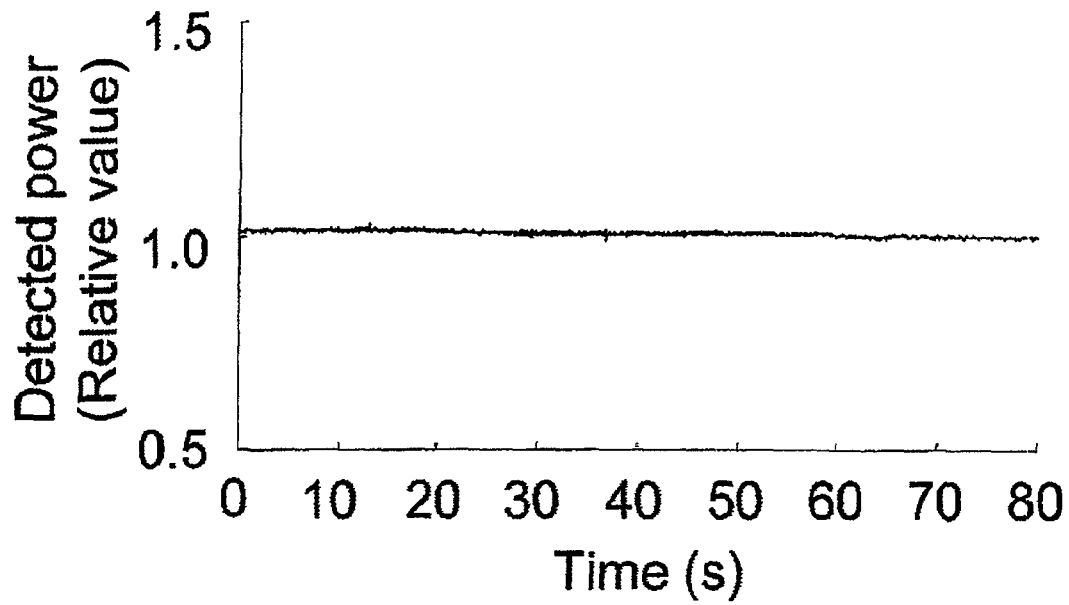
[Figure 30]
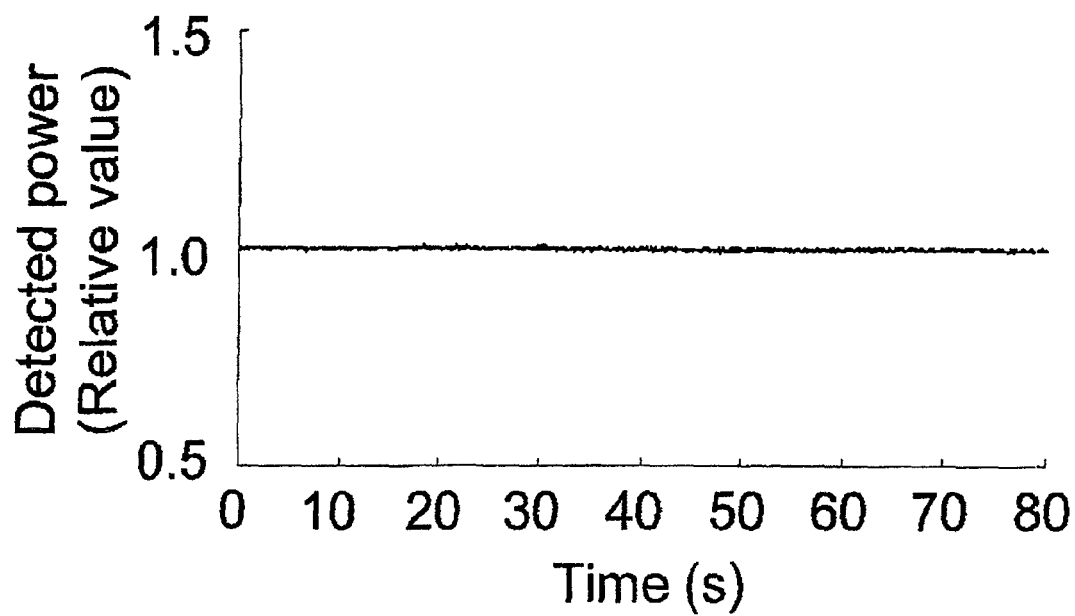

[Figure 31]
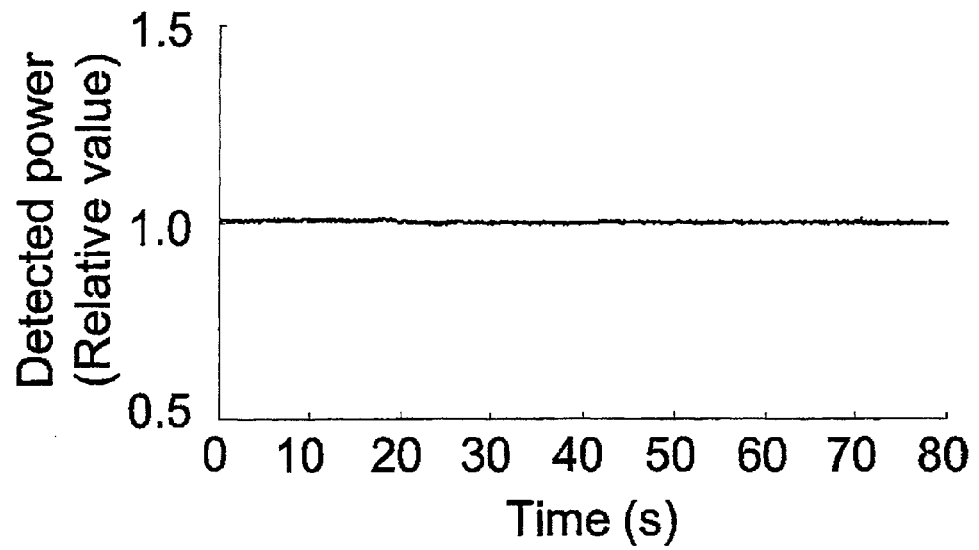
[Figure 32]
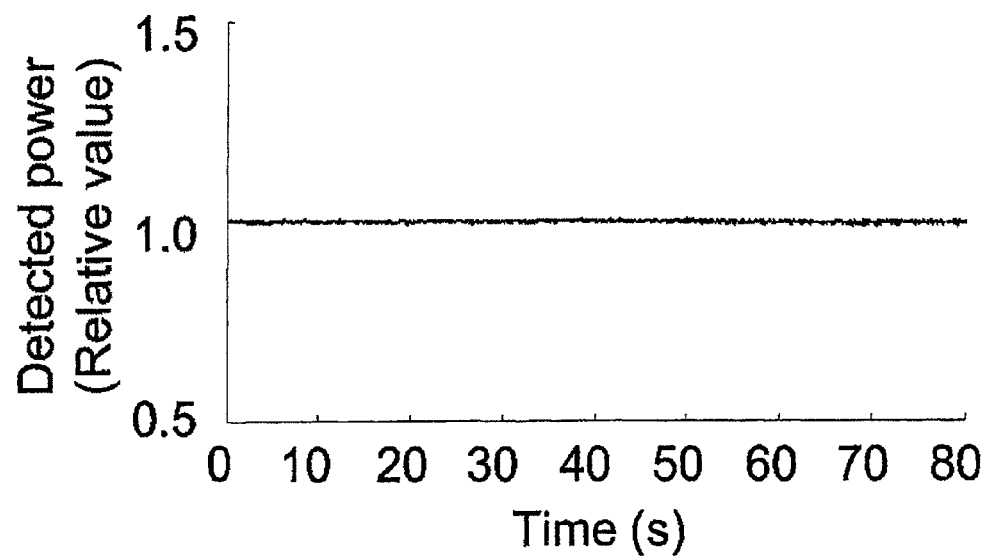

[Figure 33]
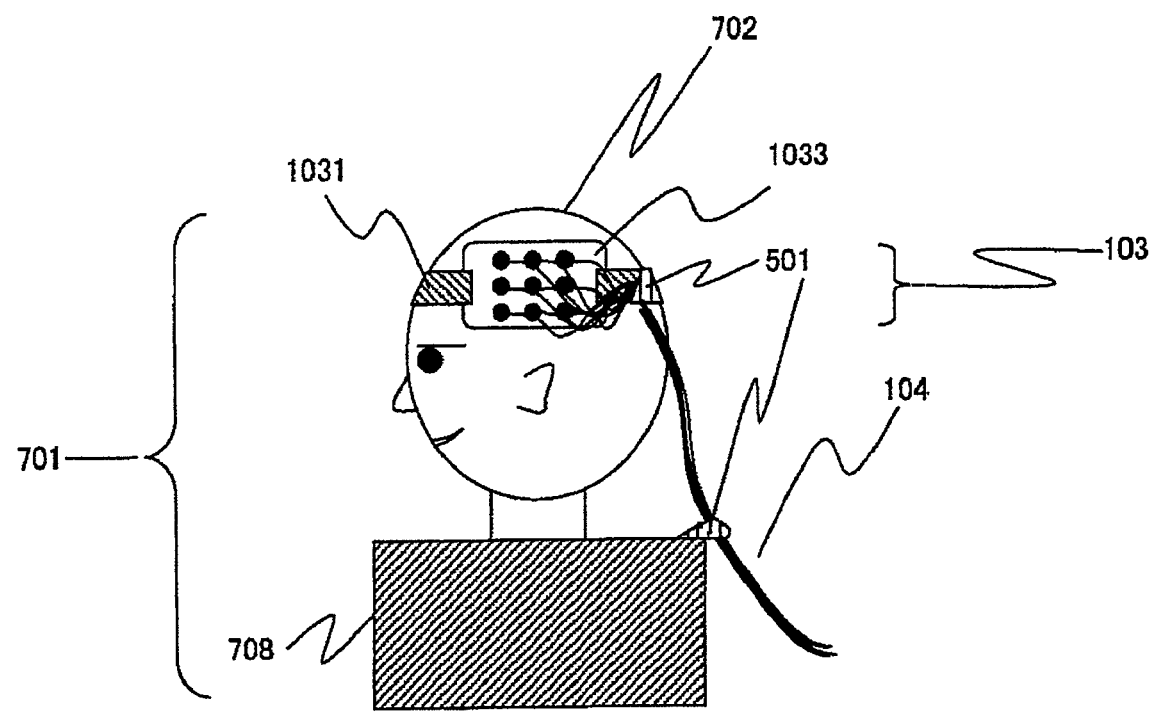

OPTICAL BIOINSTRUMENTATION DEVICES

FIELD OF THE INVENTION

The present invention relates to an optical bioinstrumentation device, which measures the information inside the living body by using light.

PRIOR ART

The apparatuses which are able to measure the information inside a living body in a simple procedure and without giving hazardous damage to a living body are used in the fields of clinical medicine and brain science. Among them, the apparatus using light is extremely effective means. The primary reason for the effectiveness of optical measurement is that the oxygen metabolism inside the living body depends on the concentrations of specific chromophores (hemoglobin, cytochrome aa3, myoglobin and others), and that the concentrations of these chromophores can be calculated from the light absorption amount. The second and the third reasons are the simplicity in handling light with the use of optic fiber, and the absence of hazardous effect on the living body as far as the amount used is within the permissible limit of safety criteria.

Optical bioinstrumentation devices, which take advantages of such optical measurement and use the light of visual to infrared wavelengths to measure the information inside the living body are described in patent documents, for example Patent 1 or Patent Document 2. The optical bioinstrumentation device described in such patent documents generates light with semiconductor laser, guides the light thus generated with optical fiber to irradiate upon a subject, detects the light which transmits or reflects from the living body, leads the light thus detected by the optic fiber to the photo diode and obtains the information about the living body from the detected amount of light, including blood circulation, hemodynamics and changes in hemoglobin.

In order to realize such optical measurement, an optical measurement probe which makes the optical fiber contact with the subject is used. This probe comprises a light irradiation part to irradiate light, a light detection part to detect the light transmitted through or reflected from the living body and a fixing member to fix the irradiation part and the detection part by disposing them in a lattice-like or a net-like arrangement. Also, the probe has a shape which enables to make the light irradiation part and the light detection part contact the subject by using a belt, elastic cord, hair band and the like. Examples of such optical measurement probe are shown in Patent Document 3. Usually multiple optical fibers are used, and the optical measurement probe having a structure to bundle such multiple optical fibers are described in Patent documents 4, 5, 6, 7, 8 and 9.

[Patent Document 1]
Japan Published unexamined patents application No. Hei 09-98972
[Patent Document 2]
Japan Published unexamined patents application No. Hei 09-149903
[Patent Document 3]
Japan Published unexamined patents application No. Hei 08□117209
[Patent Document 4]
Japan Published unexamined patents application No. 2001-286449
[Patent Document 5]
Japan Published unexamined patents application No. 2002-11012
[Patent Document 6]
Japan Published unexamined patents application No. 2003-322612
[Patent Document 7]
Japan Published unexamined patents application No. 2004-205493
[Patent Document 8]
Japan Published unexamined patents application No. 2004-248961
[Patent Document 9]
Japan Published unexamined utility model application No. Hei 5-93403

OBJECT TO BE ACHIEVED BY THE INVENTION

In the optical measurement, unlike the case where the subject to be measured is an inorganic sample, it is difficult to immobilize the subject, which is a living body, during measurement. If the subject moves, the optical measurement probe that is in contact with the subject may be dislocated or separated, thereby preventing accurate measurement. Changes in measurement data caused by the displacement of the optical measurement probe may constitute one of the causes of noise undesirable for the intended purpose to the measurement data which reflect the information inside the living body. However, in practice, since it is impossible to immobilize the subject completely during measurement, an optical bioinstrumentation device equipped with a robust measurement probe against the movement of the subject is necessary in order to improve the reliability of the measured data.

MEANS FOR SOLVING THE PROBLEMS

The aforementioned problems can be solved by fixing the parts other than the tips of the optical fibers for irradiation and detection on the fixing member for fixing the tip of the optical fibers for irradiation and detection, or by fixing the optical fiber on the fixing member and the subject, or by fixing the optical fiber at two or more positions on the subject. Specifically, a robust optical bioinstrumentation device against the movement of the subject can be achieved with the following configuration.

(1) An optical bioinstrumentation device for measuring hemodynamic changes in a head of a subject, comprising the plural number of optical fibers for irradiating light on the head of the subject, the plural number of optical fibers for detecting light transmitted inside the head, a fixing member for fixing the end of the plural number of optical fibers for irradiation and the end of the plural number of optical fibers for detection, and the plural number of means for fixing the parts other than the tip of the plural number of optical fibers for irradiation and the parts other than the tip of the plural number of optical fibers for detection on the fixing member, wherein the means for fixing optical fibers are installed respectively on the plural number of optical fibers for irradiation and the plural number of optical fibers for detection.

(2) An optical bioinstrumentation device for measuring hemodynamic changes in a head of a subject, comprising the plural number of optical fibers for irradiating the light on the head of the subject, the plural number of optical fibers for detecting the light transmitted inside the head, a fixing member for fixing the tip of the plural number of optical fibers for irradiation and the tip of the plural number of optical fibers for detection on the head, the plural number of first means for fixing the parts other than the tip of the multiple number of optical fibers for irradiation and the parts other than the tip of the plural number of optical fibers for detection on the fixing member, and the second means for fixing the parts other than the tip of the plural optical fibers for irradiation and the parts other than the tip of the plural numbers of optical fibers for detection on the subject.

(3) An optical bioinstrumentation device for measuring hemodynamic changes in a head of a subject, comprising the plural number of optical fibers for irradiating the light on the head of the subject, the plural number of optical fibers for detecting the light transmitting inside the aforementioned head, a fixing member for fixing the tip of the plural number of optical fibers for irradiation and the tip of the plural optical fibers for detection on the head, the first means for fixing the parts other than the tip of the plural number of optical fibers for irradiation and the parts other than the tip of the plural number of optical fibers for detection at the first position on the subject, and the second means for fixing the parts other than the tip of the plural number of optical fibers for irradiation and the parts other than the tip of the plural number of optical fibers for detection on the second position on the subject.

EFFECT OF THE INVENTION

According to the present invention, there can be provided measurement data which reflects information inside the living body more correctly with less noise than the conventional data, even the subject moves while measuring the information by using light.

BRIEF DESCRIPTION OF THE DRAWINGS

FIG. 1 is an overall block diagram of the optical bioinstrumentation device to which the present invention is applied.

FIG. 2 shows the first embodiment of the present invention.

FIG. 3 shows the details of means for fixing optical fibers, which is a part of FIG. 2.

FIG. 4 shows the details of means for fixing optical fibers, which is a part of FIG. 2.

FIG. 5 shows another embodiment of the optical measurement probe, which is a part of FIG. 1.

FIG. 6 shows another embodiment of the optical measurement probe, which is a part of FIG. 1.

FIG. 7 shows another embodiment of the optical measurement probe, which is a part of FIG. 1.

FIG. 8 shows another embodiment of the optical measurement probe, which is a part of FIG. 1.

FIG. 9 shows the details of means for fixing optical fibers, which is a part of FIG. 8.

FIG. 10 shows another embodiment of the optical measurement probe, which is a part of FIG. 1.

FIG. 11 shows the second embodiment of the present invention.

FIG. 12 shows the details of means for fixing optical fibers and a fixing belt, which is a part of FIG. 11.

FIG. 13 shows another embodiment of means for fixing optical fibers and a fixing belt, which is a part of FIG. 11.

FIG. 14 shows the details of the means for fixing optical fibers shown in FIG. 13.

FIG. 15 shows the details of the means for fixing optical fibers shown in FIG. 13.

FIG. 16 shows another example of the embodiment shown in FIG. 11.

FIG. 17 shows another example of the embodiment shown in FIG. 11.

FIG. 18 shows another example of the embodiment shown in FIG. 11.

FIG. 19 shows another example of the embodiment shown in FIG. 11.

FIG. 20 shows the motion noise evaluation device.

FIG. 21 shows the evaluation device equipped with the optical measurement probe.

FIG. 22 shows the status in which the optic fibers are fixed on the fixing member of the optical measurement probe with the means for fixing optical fibers in FIG. 21.

FIG. 23 shows the status in which the optical fibers are fixed with the means for fixing optical fibers on the fixing member of the optical measurement probe and the fixing belt which is wound around the head part of the evaluation apparatus in FIG. 21.

FIG. 24 shows the status in which the optical fiber are fixed with the means for fixing optical fibers on the shoulder part of the evaluation device of FIG. 21.

FIG. 25 shows results of evaluation when the motion noise evaluation apparatus was moved in the conditions shown in FIG. 21.

FIG. 26 shows results of evaluation when the motion noise evaluation apparatus was moved on the conditions shown in FIG. 22.

FIG. 27 shows results of evaluation when the motion noise evaluation apparatus was moved in the conditions shown in FIG. 23.

FIG. 28 shows results of evaluation when the motion noise evaluation apparatus was moved on the conditions shown in FIG. 24.

FIG. 29 shows results of evaluation when the motion noise evaluation apparatus was moved in the conditions combining those shown in FIG. 22 and FIG. 23 and without using the means for fixing optical fibers on the fixing member.

FIG. 30 shows results of evaluation when the motion noise evaluation apparatus was moved in the conditions combining those shown in FIG. 22 and FIG. 24 and without using the means for fixing optical fibers on the fixing member.

FIG. 31 shows results of evaluation when the motion noise evaluation apparatus was moved in the conditions combining those shown in FIG. 23 and FIG. 24 and without using the means for fixing optical fibers on the fixing member.

FIG. 32 shows results of evaluation when the motion noise evaluation apparatus was moved in the conditions combining those shown in FIGS. 22-24.

FIG. 33 shows the status in which the optical fibers are fixed on the fixing belt of the optical measurement probe (the fixing belt is wound around the head part of the evaluation apparatus in FIG. 21) and the shoulder part of the evaluation apparatus with means for fixing optical fibers.

BEST MODE FOR CARRYING OUT THE INVENTION

Embodiments of the present invention will be explained below with the reference of the attached drawings.

EXAMPLE 1

The first embodiment of the optical bioinstrumentation device of the present invention will be explained. FIG. 1 is a schematic drawing showing the configuration of equipment of the optical bioinstrumentation device of the present invention. The optical bioinstrumentation device 100 is controlled by the information processing part 102 equipped in the main unit 101 of the device, and obtains information inside the living body by emitting and receiving the light at one ends of optical fibers 104, which are connected with a non-illustrated light emission part and a non-illustrated light receiving part, both of which are installed on the back of the main unit of the device 101, and by irradiating light on the subject and detecting light at the other ends of the optical fibers 104 which are fixed on the optical measurement probe equipped in the subject. In order to protect the optical fibers 104, the plural number of optical fibers 104 may be protected by using an optical fiber cover 1041. In order to improve the ease of handling, the optical fibers 104 or the optical fiber cover 1041 may be hung from an arm 105 fixed on the main unit 101 of the device. Input devices including a keyboard 1022 and a mouse 1023 and □ display device 1024 including a monitor, which are connected with the information processing part 102, enable operators to operate and control the optical bioinstrumentation device 100. The display device 1024 displays the results of measurement inside the living body of the subject and the information necessary for the operators to operate and control the apparatus. An optical measurement probe 103 comprises a fixing member 1033 and a fixing belt 1031 for fixing the probe on the subject, optical fiber fixing sockets 1032 for fixing the tips of the optical fibers 104 on the fixing member 1033 and means 300 for fixing the optical fibers 104 on the fixing member 1033 in order to suppress the noise caused by the movement of the subject and superimposed to the measurement signals.

The means for fixing optical fibers 300 will be described with reference to the detailed illustration of the optical measurement probe 103 in FIG. 2. Each optical fiber 104 is fixed on the fixing member 1033 by the fixture 3011, an example of the means for fixing optical fibers 300, near each optical fiber fixing socket 1032. The fixture 3011 may be of an adhesive member such as adhesive tape and, as shown in FIG. 3, can fix the optical fiber 104 near the optical fiber fixing socket 1032. FIG. 4 shows an example in which the fixture 3011 is replaced by the fixture 3012 comprising a loop fastener tape 308a adhered or sutured on fabric, plastic, paper or the like. By pasting the loop fastener tape 308b adhered or sutured on the fixing member 1033 and the loop fastener tape 308a adhered or sutured on the fixture 3012, the optical fiber 104 can be fixed near the optical fiber fixing socket 1032.

The effects of the above mentioned fixtures 3011 and 3012 were confirmed by the following evaluation method. As shown in FIG. 20, a motion noise evaluation apparatus 701 equipped with a puppet head was produced. The puppet head 702 can move in the movement direction 7011. The evaluation apparatus 701 can be useful to evaluate the robustness of the probe to the movement of the puppet head, i.e., the subject, by equipping the optical measurement probe 103 on the puppet head 702 as shown in FIG. 21. FIG. 21 shows an example in which the optical measurement probe 103 without having the fixtures 3011 and 3012 is installed on the puppet head 702. The measurement data obtained while the puppet head 702 was put into motion under these conditions is shown in FIG. 25. It is known that the puppet head 702 moves in the periods between 20 and 30 seconds and between 60 and 70 seconds after the start of the measurement, and the measurement data varies greatly with the movement. FIG. 22, on the other hand, shows another example, in which the optical measurement probe 103 having the fixture 3011 of the present invention is installed on the puppet head 702, and FIG. 26 shows the measurement data taken while the puppet head was moved under the same conditions to those shown in FIG. 21. It was revealed that the installation of the fixture 3011 had the effect to dramatically reduce the measurement noise caused by the movement of the subject.

EXAMPLE 2

FIG. 5 shows fixtures 302, as an example of the means for fixing optical fibers 300. The fixture 302 is devised to be able to fix three optical fibers constituting one line of a 3×3 matrix, for example, with one fixture, rather than by installing the fixture 3011 or the fixture 3012 separately for each optical fiber. In this example, the fixture 302 and the fixing member 1033 are to be fixed and combined at both ends of the fixture 302 and a middle position between individual optical fibers. In this example, the plural number of optical fibers can be pressed at the same time. In addition, similar effects with those obtained by the fixture 3011 and the fixture 3012 can be obtained.

EXAMPLE 3

FIG. 6 and FIG. 7 show other embodiments of the fixture 3011 and the fixture 3012. In this embodiment, as shown in FIG. 6 and FIG. 7, the plural number of optical fibers 104 fixed on the plural number of closely arranged fixing sockets 1032 are fixed by using the fixture 3011 or the fixture 3012 on the fixing member 1033 at one position. In this embodiment, the fixing position with the fixture can be set arbitrarily in accordance with the hardness of the optical fiber 104, the shape of the fixing member 1033, the posture of the subject and/or the procedure of measurement.

EXAMPLE 4

FIG. 8 and FIG. 9 show the fixture 303, as an example of the means for fixing optical fibers 300. The fixture 303 is made of solid material such as elastic plastic, or of the same material with that of the fixing member 1033. One end of the fixture 303 is fixed or adhered on the fixing member 1033, while a nail-shaped hook is formed at the other end, and there is a gap between this hook and the fixing member 1033. The optical fiber 104 can be inserted from this gap and fixed on the fixing member 1033 by taking the advantage of elasticity of the fixture 303. Thus, similar effects with those obtained by the fixture 3011 and the fixture 3012 can be obtained.

EXAMPLE 5

In FIG. 10, the fixing member 1034 is made of gel and has excellent feeling of contact for the subject. The optical fiber 104 is laid within the grooves inside this fixing member 1034. On the fixing member 1034, the optic fiber 104 can be fixed by using the separate type fixture 304. The optical fiber 104 laid in the grooves on the top part 304a of the separate type fixture 304 are held by the bottom part 304a, whereby the separate type fixture 304 is fixed on the fixing member 1034. This provides similar effects with those obtained by the fixture 3011 and the fixture 3012.

EXAMPLE 6

Next, the second embodiment of the optical bioinstrumentation device of the present invention is explained below. FIG. 11 shows an example where the optical fibers are fixed on the fixing member of the optical measurement probe by the use of the plural number of the first means for fixing optical fibers and on the subject by the use of the second means for fixing optical fibers. The first means for fixing optical fibers can be any of the fixture 3011, fixture 3012, fixture 302, fixture 303 or fixture 304 which have been explained in detail in the aforementioned first embodiment, and is expressed collectively as the first fixture 300. The fixing member 1033 is fixed on the head of the subject 520 with the fixing belt 1031, and on this fixing member 1033 the optical fiber 104 is fixed with the first fixture 300. The characteristic of this embodiment is that the optical fibers 104 are also fixed on the shoulder of the subject 520 with the second fixture 500. The second fixture 500 can be fixed on the wearing member such as the fixing belt 507 wound around the shoulder of the subject 520.

By reference to FIG. 12, the example in which the second fixture 500 comprises a fixture 501 and a fixture belt 507 is explained. The fixture belt 507 is made of such material as fabric and paper, which is easily wound around the subject 520, and on both ends of which the loop fastener tape 508 is adhered or sutured. The fixing belt 507 is wound around the shoulder of the subject 520, and fixed on the subject 520 with the loop fastener tape 508. The fixture 501 is made of such material as fabric, paper or plastic, and can fix the optical fiber on the fixture belt 507 with the loop faster or the like, in a similar manner as that using the fixture 3012 shown in FIG. 4.

The effects of the first fixture 300 and the fixture 501 were confirmed as follows. As shown in FIG. 24, the evaluation was performed as in Example 1 by installing the optical measurement probe 103 on the puppet head 702 of the motion noise evaluation apparatus 701, by fixing the optical fibers 104 on the fixing member 1033 with the fixtures 3011, that is, an example of the first means for fixing optical fibers 300, and further by fixing the optical fibers 104 at the position corresponding to the shoulder part of the evaluation device with the fixture 501. The evaluation performed in said conditions provided stable data as shown in FIG. 30. Similarly, the evaluation, which used only the fixture 501 but not the first fixture 3011, produced the results shown in FIG. 28. It was known from these evaluations that the use of the first and the second means for fixing optical fibers could dramatically reduce the measurement noise caused by the movement of the subject.

EXAMPLE 7

FIG. 13 shows another example of the second means for fixing optical fibers 500 comprising a fixture 502 and a fixture belt 507. On the fixture 502 made of hard material such as plastic, the protrusions 502a and the recesses 502b are formed on the side facing the side that is in contact with the fixing belt 507, and the fixture 502 is fixed on the fixture belt 507 as being adhered or sutured. As shown in FIG. 14, by entangling the optical fibers 104 with the protrusion 502a of the fixture 502, the optical fiber can be immobilized and firmly fixed. FIG. 15 shows a drawing of FIG. 13 viewed from a different angle. It was found that the fixture 502 provides similar effects with those by the fixture 501.

EXAMPLE 8

FIG. 16 shows an example in which the optical fibers 104 are fixed on the fixing member 1033 of the optical measurement probe 103 with the first means for fixing optical fibers 300, the fixture belt 507 is fixed on the chest of the subject 520, and the optical fibers 104 are fixed on the back of the subject 520 with the fixture 501 or the fixture 502. FIG. 17 shows an example, in which the fixture belt 507 is fixed on the abdominal part of the subject and the optical fibers 104 are fixed on the hip of the subject with the fixture 501 or the fixture 502. FIG. 18 shows an example, in which one of the fixture belts 507 is fixed around the shoulder and another around the abdominal part of the subject. The optical fibers 104 are fixed on the shoulder and the abdominal part of the subject with the fixture 501 or the fixture 502. In all of Examples shown in FIGS. 16, 17 and 18, similar effect with that of the aforementioned Example 6 was obtained.

EXAMPLE 9

FIG. 19 shows an example, in which the optical fiber 104 is fixed on the fixing member 1033 of the optical measurement probe 103 with the first means for fixing optical fibers 300 (including 3011, 302, 303 and others), the optical fibers 104 are also fixed on the fixing belt 1031 by placing the fixture 501 or the fixture 502 on it, and further the optical fibers are fixed with the fixing belts wound around the shoulder and the hip of the subject and the fixture 501 or the fixture 502.

The effect of the fixture 501 or the fixture 502 equipped in the fixing belt wound around the head was confirmed as follows. As shown in FIG. 23, the evaluation was performed like in Example 1, in the conditions, in which the optical measurement probe 103 was equipped on the puppet head 702 of the evaluation device 701, the optical fibers 104 were fixed on the fixing member 1033 with the fixture 3011, and the optical fibers 104 were fixed on the fixing member 1033 with the fixture 3011. As the result, stable data was obtained as shown in FIG. 29. In the conditions in which only the fixture 501 was used but not the first fixture 3011 in FIG. 23, there was provided the results shown in FIG. 27. In comparison with the case shown in FIG. 25, the effect was observed when the optical fiber 104 was fixed only on the fixing belt 1031 with the fixture 501. However, more stable data was obtained as shown in FIG. 20 by using the first and the second means for fixing optical fibers in combination.

EXAMPLE 10

The third embodiment of the optical bioinstrumentation device of the present invention is explained below. As shown in FIG. 33, the optical fibers 104 are fixed on the head of the subject with the fixing belt 1031 and the fixture 501, without using the fixture 3011 for the fixing member 1033, and at the position corresponding to the shoulder of the subject with the fixing belt 507 and the fixture 501. Namely, the optical fibers are fixed at two or more positions of the subject. Under the conditions shown in FIG. 33, the results shown in FIG. 31 were provided. These resulted data are very stable, containing no noise caused by the movement of the puppet head.

The evaluation was performed in a similar manner as that in Example 1, that is, the optical measurement probe 103 was equipped on the puppet head 702 of the motion noise evaluation apparatus 701, the optical fibers 104 were fixed on the fixing member 1033 with the fixture 3011, the optical fibers 104 were also fixed on the fixing belt 1031 with the fixture 501, and the optical fibers were further fixed at the position corresponding to the shoulder on the main unit 708 of the motion noise evaluation apparatus. As the results, data shown in FIG. 32 was obtained. It is known from the results that, as shown in FIG. 19, means for fixing optical fibers which fixes the optical fibers 104 on the fixing member 1033 and at two or more positions of the subject is effective to provide the resulted data which is less likely to be affected by the movement of the subject 520.

INDUSTRIAL APPLICABILITY

The optical bioinstrumentation device of the present invention can perform measurement without restraining a subject of the measurement, but allowing the subject in free posture, and yet suppress the generation of the noise caused by the body movement of the subject and contained in the measurement signals. Moreover, because the device is not necessarily of large size, the optical bioinstrumentation device of the present invention may be used in many medical, welfare and research institutions.

DESCRIPTION OF NOTATIONS

100: Optical bioinstrumentation device, 101: Main unit of the device, 102: Information processing device, 1022: Keyboard, 1023: Mouse, 1024: Display device, 103: Optical measurement probe, 1031: Fixing belt, 1032: optical fiber fixing socket, 1033: Fixing member, 1034: Fixing member using gel, 104: Optical fiber, 1041: Optical fiber cover, 105: Arm, 300: Fixture (means for fixing optical fibers), 3011: Fixture, 3012: Fixture, 302: Fixture, 303: Fixture, 304: Fixture, 304*a*: Upper part of the fixture, 304*b*: Lower part of the fixture, 308*a*: Loop fastener tape, 308*b*: Loop fastener tape, 500: Second fixture (means for fixing optical fibers), 501: Second fixture, 502: Second fixture, 507: Fixture belt, 508: Loop fastener tape, 520: Subject, 701: Motion noise evaluation apparatus, 7011: Puppet head moving direction, 702: Puppet head, 708: Main unit of evaluation apparatus

The invention claimed is:

1. An optical bioinstrumentation device for measuring hemodynamic changes in a head of a subject, comprising:
   a plural number of optical fibers configured to irradiate light onto the head of the subject;
   a plural number of optical fibers configured to detect light which is transmitted inside the head;
   a fixing member for holding tips of the plural number of optical fibers configured to irradiate and tips of the plural number of optical fibers configured to detect; and
   a plural number of holding members for fixing a first part of the optical fibers, other than the tips of the plural number of optical fibers configured to irradiate, and a first part of the optical fibers other than the tips of the plural number of optical fibers configured to detect, on the fixing member respectively to prevent movement of the optical fibers relative to the fixing member;
   wherein the fixing member is configured to be fixed on the head of the subject, and the holding members for fixing optical fibers are installed for each of the plural number of optical fibers configured to irradiate and the plural number of optical fibers configured to detect; and
   wherein the holding members for fixing optical fibers further comprises a second holding member for fixing optical fibers to fix a second part of the optical fibers other than the tip of the plural number of optical fibers configured to irradiate and a second part of the optical fibers other than the tip of the plural number of optical fibers configured to detect on a wearing member which the subject wears to prevent movement of the optical fibers relative to the wearing member,
   wherein each of the holding members has a hook or a protrusion, which entangles the part of the optical fibers other than the tip of the plural number of optical fibers configured to irradiate and the part of the optical fibers other than the tip of the plural number of the optical fibers configured to detect.

2. The optical bioinstrumentation device according to claim 1, wherein the second holding member is configured to fix the plural number of optical fibers.

3. The optical bioinstrumentation device according to claim 1, wherein the second holding member is configured to be worn on a part of the body other than the head.

4. An optical bioinstrumentation device for measuring hemodynamic changes in a head of a subject, comprising:
   a plural number of optical fibers configured to irradiate light onto the head of the subject;
   a plural number of optical fibers configured to detect light which is transmitted inside the head;
   a fixing member configured to be fixed on the head of the subject for holding tips of the plural number of optical fibers configured to irradiate and tips of the plural number of optical fibers configured to detect;
   a first holding member for fixing a first part of the optical fibers other than the tips of the plural number of optical fibers configured to irradiate, and a first part of the optical fibers other than the tips of the plural number of optical fibers configured to detect on the fixing member to prevent movement of the of the optical fibers relative to the fixing member; and
   a second holding member for fixing a second part of the optical fibers other than the tips of the plural number of optical fibers configured to irradiate and a second part of the optical fibers other than the tips of the plural number of optical fibers configured to detect on a wearing member which the subject wears to prevent movement of the optical fibers relative to the wearing member,
   wherein each of the first or second holding members has a hook or a protrusion which entangles the first or second part of the optical fibers other than the tip of the plural number of optical fibers configured to irradiate and the first or second part of the optical fibers other than the tip of the plural number of the optical fibers configured to detect,
   wherein the first and the second holding members for fixing optical fibers include protrusions, and fix optical fibers by entangling the parts other than the tip of the plural number of optical fibers with the protrusions.

5. An optical bioinstrumentation device for measuring hemodynamic changes in a head of a subject, comprising:
   a plural number of optical fibers configured to irradiate light onto the head of a subject;
   a plural number of optical fibers configured to detect light which is transmitted inside the head;
   a fixing member configured to be fixed on the head of the subject for holding tips of the plural number of optical fibers configured to irradiate and tips of the plural number of optical fibers configured to detect;
   a first holding member for fixing a first part of the optical fibers other than the tips of the plural number of optical fibers configured to irradiate, and a first part of the optical fibers other than the tips of the plural number of optical fibers configured to detect on a first position on the subject to prevent movement of the optical fibers relative the first position of the subject; and
   a second holding member for fixing a second part of the optical fibers other than the tips of the plural number of optical fibers configured to irradiate and a second part of the optical fibers other than the tips of the plural number of optical fibers configured to detect on a second position on the subject;

wherein the second holding member for fixing optical fibers is fixed on a wearing member which the subject wears to prevent movement of the optical fibers relative to the wearing member, wherein each of the first or second holding members has a hook or a protrusion which entangles the first or second part of the optical fibers other than the tip of the plural number of optical fibers configured to irradiate and the first or second part of the optical fibers other than the tip of the plural number of the optical fibers configured to detect, wherein the first and the second holding members for fixing optical fibers include protrusions, and fix optical fibers by entangling the parts other than the tip of the plural number of optical fibers with the protrusions.

* * * * *